United States Patent
Amanullah

(10) Patent No.: US 9,772,320 B2
(45) Date of Patent: Sep. 26, 2017

(54) CLASSIFICATION SCHEME OF SIZED BRIDGING MATERIALS FOR SUPERIOR DRILL-IN FLUID DESIGN

(71) Applicant: Md. Amanullah, Dhahran (SA)

(72) Inventor: Md. Amanullah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 730 days.

(21) Appl. No.: 13/646,180

(22) Filed: Oct. 5, 2012

(65) Prior Publication Data

US 2013/0125677 A1   May 23, 2013

Related U.S. Application Data

(60) Provisional application No. 61/544,299, filed on Oct. 7, 2011.

(51) Int. Cl.
| | | |
|---|---|---|
| *G01N 33/24* | (2006.01) | |
| *G01N 33/28* | (2006.01) | |
| *G01N 15/02* | (2006.01) | |
| *C09K 8/03* | (2006.01) | |

(52) U.S. Cl.
CPC ......... *G01N 33/2823* (2013.01); *C09K 8/032* (2013.01); *G01N 15/0211* (2013.01); *C09K 2208/18* (2013.01)

(58) Field of Classification Search
USPC ........................................ 73/866, 821, 865.5
See application file for complete search history.

(56) References Cited

U.S. PATENT DOCUMENTS

| 4,677,843 | A | 7/1987 | Schroeder |
| 6,490,527 | B1 | 12/2002 | Utt |
| 6,751,557 | B1 | 6/2004 | Shehab et al. |
| 2009/0103677 | A1 | 4/2009 | Wood et al. |
| 2010/0313645 | A1* | 12/2010 | Doman et al. ............ 73/152.04 |
| 2012/0079888 | A1 | 4/2012 | Amanullah et al. |

FOREIGN PATENT DOCUMENTS

WO WO2009105469 A2   8/2009
WO WO2010048276 A2   10/2009

OTHER PUBLICATIONS

The Aramco Method, Its drilling and production engineering significance, Md, Amanullah , May 15, 2011.*
"Designing Drill-in Fluids by Using Ideal Packing Technique", 2007, Feng et al.*

(Continued)

*Primary Examiner* — Paul West
*Assistant Examiner* — Xin Zhong
(74) *Attorney, Agent, or Firm* — Bracewell LLP; Constance G. Rhebergen; Keith R. Derrington

(57) ABSTRACT

A classification scheme for classifying sized bridging materials is disclosed. The scheme identifies a durability metric for the sized bridging materials. The scheme then identifies a value range having a higher relative strength and a lower relative strength. The sized bridging materials may then be tested according to the durability metric and associated with a relative strength based on the durability metric determined during the test.

20 Claims, 11 Drawing Sheets

| BROAD CATEGORY | CLASS RANKING SYMBOL | CLASS RANKING | $ShF_{D50}$ (D50 SHIFT FACTOR) | | |
|---|---|---|---|---|---|
| | | | ABSOLUTE VALUES | | |
| TOUGH SBM | SBM - ET | EXTREMELY TOUGH SBM | 0 - 0.05 | SBM PARTICLES THAT HAVE A D50 SHIFT FACTOR GREATER THAN OR EQUAL TO 0.0 AND LESS THAN OR EQUAL TO 0.05 WHEN TESTED IN ACCORDANCE WITH THE PROCEDURE DESCRIBED HEREIN | |
| | SBM - VT | VERY TOUGH SBM | 0.05 - 0.01 | SBM PARTICLES THAT HAVE A D50 SHIFT FACTOR GREATER THAN 0.05 AND LESS THAN OR EQUAL TO 0.01 WHEN TESTED IN ACCORDANCE WITH THE PROCEDURE DESCRIBED HEREIN | |
| | SBM - MT | MODERATELY TOUGH SBM | 0.1 - 0.2 | SBM PARTICLES THAT HAVE A D50 SHIFT FACTOR GREATER THAN 0.1 AND LESS THAN OR EQUAL TO 0.2 WHEN TESTED IN ACCORDANCE WITH THE PROCEDURE DESCRIBED HEREIN | |
| | SBM - ST | SLIGHTLY TOUGH SBM | 0.2 - 0.3 | SBM PARTICLES THAT HAVE A D50 SHIFT FACTOR GREATER THAN 0.2 AND LESS THAN OR EQUAL TO 0.3 WHEN TESTED IN ACCORDANCE WITH THE PROCEDURE DESCRIBED HEREIN | |
| WEAK SBM | SBM - W | WEAK SBM | SBM PARTICLES THAT HAVE A D50 SHIFT FACTOR GREATER THAN 0.3 AND LESS THAN OR EQUAL TO 0.5 WHEN TESTED IN ACCORDANCE WITH THE PROCEDURE DESCRIBE HEREIN | 0.3 - 0.5 | |
| | SBM - FW | FAIRLY WEAK SBM | SBM PARTICLES THAT HAVE A D50 SHIFT FACTOR GREATER THAN 0.5 AND LESS THAN OR EQUAL TO 0.7 WHEN TESTED IN ACCORDANCE WITH THE PROCEDURE DESCRIBED HEREIN | 0.5 - 0.7 | |
| | SBM - VW | VERY WEAK SBM | SBM PARTICLES THAT HAVE A D50 SHIFT FACTOR GREATER THAN 0.7 AND LESS THAN OR EQUAL TO 0.9 WHEN TESTED IN ACCORDANCE WITH THE PROCEDURE DESCRIBED HEREIN | 0.7 - 0.9 | |
| | SBM - EW | EXTREMELY WEAK SBM | SBM PARTICLES THAT HAVE A D50 SHIFT FACTOR GREATER THAN 0.9 BUT LESS THAN 1 WHEN TESTED IN ACCORDANCE WITH THE PROCEDURE DESCRIBED HEREIN | 0.9 - 1 | |

(56) References Cited

OTHER PUBLICATIONS

"Influence of suspension stability on wet grinding for production of mineral nanoparticles" by Sakthivel et al., 2008 Chinese Society of Particuology and Institute of Process Engineering, Chinese Academy of Sciences. Published by Elsevier B.V.*

"Particle Size Analysis for Drilling in Petroleum Industry" by Nicolas Marchet, Feb./Mar. 2009.*

PCT International Search Report and The Written Opinion of the International Searching Authority dated Jan. 4, 2013; International Application No. PCT/US2012/058945; International Filing Date: Oct. 5, 2012.

Amanullah, Md., et al., The Aramco Method—Its Drilling and Production Engineering Significance, SPE/DGS Saudi Arabia Technical Symposium and Exhibition held in Al-Khobar, Saudi Arabia, May 15-18, 2011, SPE 149103, 2011, Society of Petroleum Engineers.

Wenqiang, F., et al., Designing Drill-In Fluid by Using Ideal Packing Techniques, School of Petroleum Engineering, China University of Petroleum, Beijing, CN, 2007, pp. 44-51, vol. 4 No. 2, Petroleum Science.

Wenwu He, Bridging Particle Size Distribution in Drilling Fluid and Formation Damage, SPE 143497 (2011).

* cited by examiner

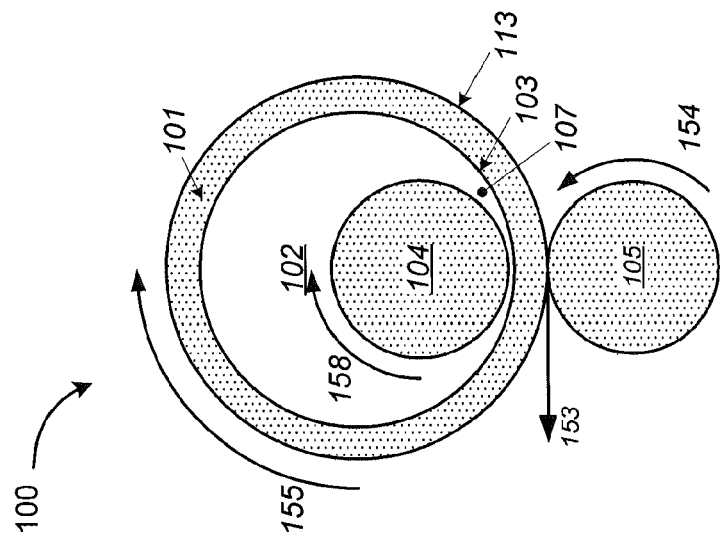
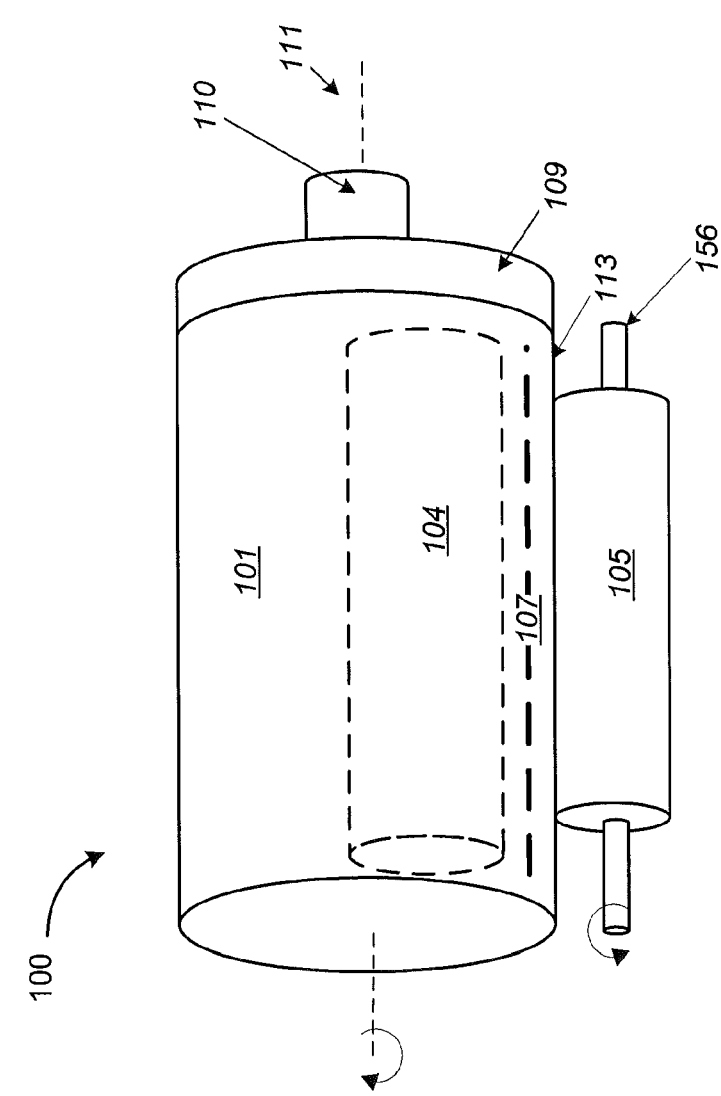

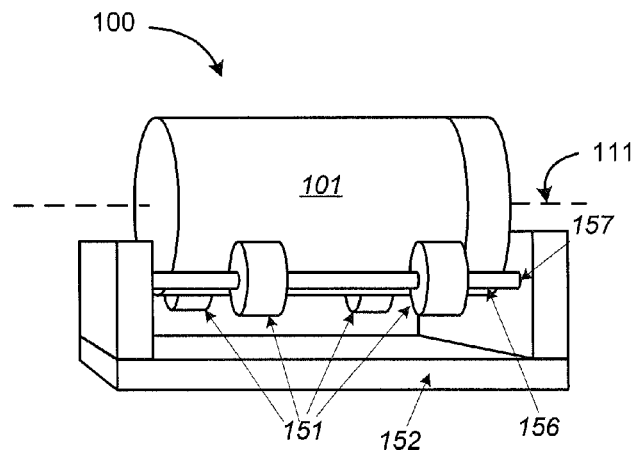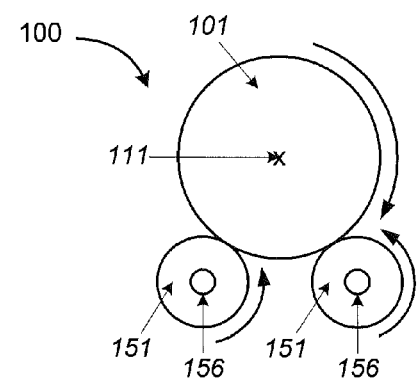
FIG. 3A  FIG. 3B
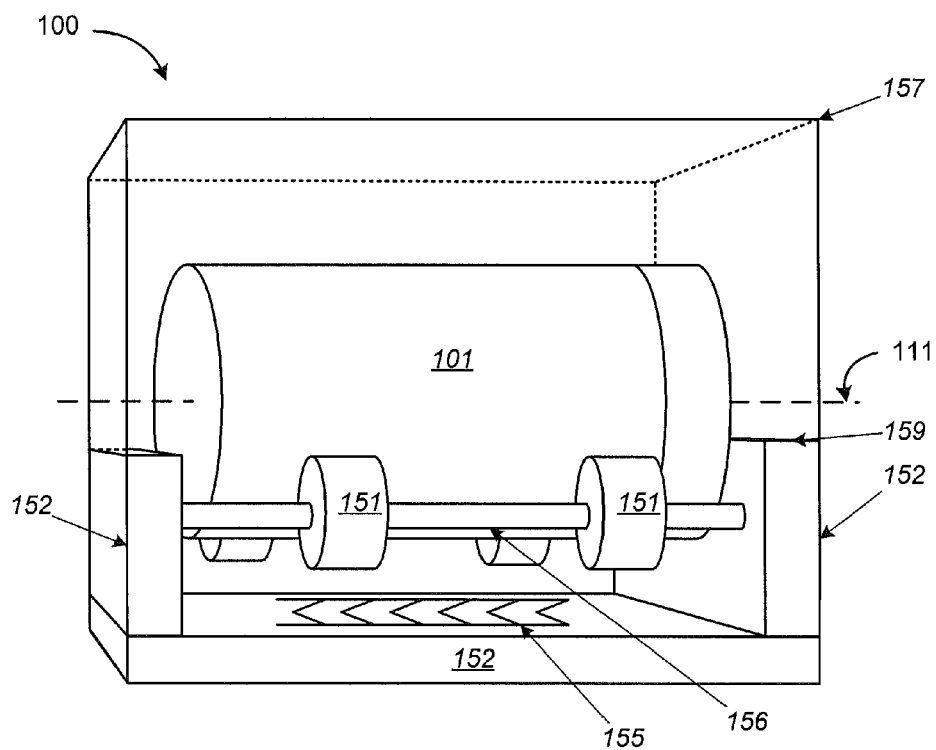
FIG. 3C

| BROAD CATEGORY | CLASS RANKING SYMBOL | CLASS RANKING | ShF$_{D50}$ (D50 SHIFT FACTOR) | |
|---|---|---|---|---|
| | | | ABSOLUTE VALUES | |
| TOUGH SBM | SBM - ET | EXTREMELY TOUGH SBM | 0 - 0.05 | SBM PARTICLES THAT HAVE A D50 SHIFT FACTOR GREATER THAN OR EQUAL TO 0.0 AND LESS THAN OR EQUAL TO 0.05 WHEN TESTED IN ACCORDANCE WITH THE PROCEDURE DESCRIBED HEREIN |
| | SBM - VT | VERY TOUGH SBM | 0.05 - 0.01 | SBM PARTICLES THAT HAVE A D50 SHIFT FACTOR GREATER THAN 0.05 AND LESS THAN OR EQUAL TO 0.01 WHEN TESTED IN ACCORDANCE WITH THE PROCEDURE DESCRIBED HEREIN |
| | SBM - MT | MODERATELY TOUGH SBM | 0.1 - 0.2 | SBM PARTICLES THAT HAVE A D50 SHIFT FACTOR GREATER THAN 0.1 AND LESS THAN OR EQUAL TO 0.2 WHEN TESTED IN ACCORDANCE WITH THE PROCEDURE DESCRIBED HEREIN |
| | SBM - ST | SLIGHTLY TOUGH SBM | 0.2 - 0.3 | SBM PARTICLES THAT HAVE A D50 SHIFT FACTOR GREATER THAN 0.2 AND LESS THAN OR EQUAL TO 0.3 WHEN TESTED IN ACCORDANCE WITH THE PROCEDURE DESCRIBED HEREIN |
| WEAK SBM | SBM - W | WEAK SBM | 0.3 - 0.5 | SBM PARTICLES THAT HAVE A D50 SHIFT FACTOR GREATER THAN 0.3 AND LESS THAN OR EQUAL TO 0.5 WHEN TESTED IN ACCORDANCE WITH THE PROCEDURE DESCRIBE HEREIN |
| | SBM - FW | FAIRLY WEAK SBM | 0.5 - 0.7 | SBM PARTICLES THAT HAVE A D50 SHIFT FACTOR GREATER THAN 0.5 AND LESS THAN OR EQUAL TO 0.7 WHEN TESTED IN ACCORDANCE WITH THE PROCEDURE DESCRIBED HEREIN |
| | SBM - VW | VERY WEAK SBM | 0.7 - 0.9 | SBM PARTICLES THAT HAVE A D50 SHIFT FACTOR GREATER THAN 0.7 AND LESS THAN OR EQUAL TO 0.9 WHEN TESTED IN ACCORDANCE WITH THE PROCEDURE DESCRIBED HEREIN |
| | SBM - EW | EXTREMELY WEAK SBM | 0.9 - 1 | SBM PARTICLES THAT HAVE A D50 SHIFT FACTOR GREATER THAN 0.9 BUT LESS THAN 1 WHEN TESTED IN ACCORDANCE WITH THE PROCEDURE DESCRIBED HEREIN |

FIG. 9

CLASSIFICATION SCHEME OF SIZED BRIDGING MATERIALS FOR SUPERIOR DRILL-IN FLUID DESIGN

This application claims priority to and the benefit of co-pending U.S. Provisional Application No. 61/544,299, by Amanullah, filed on Oct. 7, 2011, entitled "Classification Scheme of Sized Bridging Materials For Superior Drill-In Fluid Design," which application is incorporated herein by reference.

BACKGROUND OF THE INVENTION

1. Field of the Invention

The present invention relates in general to drill-in fluids used in oil and gas drilling and, in particular, to a sized bridging materials classification scheme for superior drill-in fluid design.

2. Brief Description of Related Art

A drill-in fluid is a special type of fluid formulated for oil and gas drilling. The drill-in fluid is pumped into a borehole while drilling through porous and permeable subsurface rock formations that store and transmit oil and gas, i.e., a reservoir. The drill-in fluid contains solid particles known as bridging materials to prevent fluid loss from the borehole to the reservoir by building a "filter cake" for preventing fluid loss into the reservoir.

Bridging materials are solid particles, typically composed of calcium carbonate ($CaCO_3$), dolomite, or marble, and are designed to "bridge" across the pore throat or fractures in the vicinity of the borehole wall. Bridging materials can produce a low-permeability mud-cake on the borehole wall to minimize fluid leak-off, eliminate spurt loss, arrest migration of fine particles ("fines") into the reservoir or formation, prevent mud-cake deposition into the formation, and inhibit near-wellbore formation damage. The fluid formulation containing the bridging materials, which may be referred to as a "mud," can be tailored to specific geological applications by tailoring the size range of the bridging materials to achieve a desired fluid density and bridging ability. For example, one can select bridging materials manufactured to certain sizes (coarse, medium, fine, and very fine) to achieve a particular size-distribution scheme corresponding to the pore throat sizes of a target reservoir.

The effectiveness of bridging materials depends on their structural durability, as they are subject to damage due to extreme conditions during the drilling operation (i.e., "downhole conditions"). For example, bridging materials can disintegrate, decompose, and disperse as a result of physical interactions with a drill bit, tool joint, reamer, stabilizer, mud motor stator and blades, and bent drill string. When the bridging materials decompose into smaller and finer particles, the intended distribution scheme is lost, destroying the desired fluid properties and bridging abilities. For example, there can be a dramatic change in the particle size distribution curve.

The smaller, finer particles resulting from the decomposition of bridging materials can also harm the drilling operation. For example, the loss of the drilling fluid's bridging ability may result in the migration of drilling fluids into the reservoir. And after migrating into the formation, the bridging materials, including the fine particles created when bridging materials decompose, can create deposits that damage the reservoir and significantly reduce the production capability of a well. Although properly sized bridging materials are very useful in plugging and sealing fractures and openings in a borehole wall to create a tight and low-permeability mud-cake, failure to maintain the intended size distribution while drilling may be a severe cause of near-wellbore formation damage.

The importance of using of a particular particle size distribution of bridging materials that is compatible to the pore throat size distribution of the target reservoir is well known to the industry. The industry is also aware of the importance of preserving the particle size distribution ("PSD") while drilling to get the maximum benefit of the drill-in fluid. To monitor and test for the particle size distribution of the drill-in fluid, the industry has developed numerous methods to determine the particle size distribution of a particular drilling fluid, in particular, a drilling fluid circulated through a wellbore. In addition, the industry may use that particle size distribution to determine whether to add additional sized bridging materials to the drilling fluid and how much to add to the drilling fluid. However, there is no industry method or standard test method to screen and evaluate different bridging materials as a part of quality control/assurance procedures or as part of selecting optimal bridging materials (i.e., materials with an optimal durability index). Horton et al. (Horton, R. L., Dobson, J. W. Jr., Tresco, K. O., Knox, D. A., Green, T. C. and Foxenberg, W. E. (2001), Enhanced Well Productivity Potential from a New High-Density Reservoir Drill-in Fluid, AADE 01-NC-OH-47) described the importance of using an optimum amount of sized bridging materials and an optimum PSD in drilling and drill-in fluids to control the thickness, porosity, and permeability of deposited mudcake, reduce the loss of mud filtrate into the near wellbore formation, and facilitate the effective cleaning of the mudcake from the borehole wall.

Siddiqui et al. (Siddiqui, M. A., Al-Ansari, A. A., Al-Afaleg, N. I., Al-Anazi, H. A., Hembling, D. E., and Bataweel, M. A. (2006), Drill-in Fluids for Multi-lateral MRC Wells in carbonate Reservoir—PSD Optimization and Best Practices Lead to High Productivity: A case Study; 2006 SPE Asia Pacific Oil and Gas Conf. & Exhb., Adelaide, Australia, 11-13 September, SPE#101169) described less-damaging water-based drill-in fluids for use in multilateral maximum reservoir contact wells. The authors optimized the particle size distribution using fine and medium-sized particles of calcium carbonate with fairly fixed median value to reduce formation damage caused by fines and polymer plugging. According to their study, the optimum ratio of fine to medium-sized calcium carbonate was 35:65 (8:15 ppb fine:medium) in 23 ppb bridging material loaded drill-in fluid. Tests conducted using a reservoir core and a dynamic mud flow loop at stimulated reservoir conditions resulted in 20% loss in return permeability in the presence of the size optimized drill-in fluid. The use of this size optimized drill-in fluid enhanced the well productivity significantly. The authors also emphasized the need for maintaining the designated particle size distribution in the drill-in fluid while drilling to maximize reservoir protection capacity.

According to Suri and Sharma (Suri, A. and Sharma, M. M. (2004)), Strategies for Sizing Particles in Drilling and Completion Fluids, SPE Journal, March, pp. 13-23, the sized particles used in drilling and completion fluids to minimize formation damage must be large enough to stay at the borehole wall and small enough to form a tight filter cake that effectively prevents the invasion and internal mudcake formation by any solids and polymers in the near wellbore reservoir. Modeling done by the authors based on this criterion demonstrated the usefulness of this criterion for quantitative determination of the particle size distribution necessary to design a drill-in fluids for a given formation permeability and overbalance pressure. According to the authors, the predictions of the model agree well with the results of mud filtration experiments.

According to Vickers et al. (Vickers S., Cowie M., Jones T., Tywnam, A. J. (2006)), a new methodology that surpasses current bridging theories to efficiently seal a varied pore throat distribution as found in natural reservoir formations, AADE 06-DF-HO-16, selection and maintenance of five different particle sizes with respect to the measured pore throat size distribution of the formation core are necessary in order to create a tightly packed mudcake on the borehole wall. This size distribution is required to match separately the different pore throat sizes to produce a "jamming effect" by bridging or filling the fracture openings and inter-particle gaps of all sizes. According to the authors, a particle size such as D90 should be less than the largest pore throat size, D75 should be less than ⅔ of the largest pore throat, D50 should be ±⅓ of the mean pore throat size, D25 should be ⅐ of the mean pore throat size, and D10 should be greater than the smallest pore throat size. Laboratory and field tests demonstrated the effectiveness of this particle size distribution pattern in bridging openings and preventing formation damage compared to other methods of particle size selection. According to the authors this method is equally applicable for both oil-based and water-based muds.

The importance of maintaining the intended particle size distribution during drilling operations highlights the need for a simple, reliable, accurate, and statistically valid method for screening, quality control, and quality assurance of bridging materials used for drill-in fluid formulation.

Variation in the composition of bridging materials is common due to different grinding procedures and equipment used in the process of manufacturing the bridging materials. Due to variations in the composition and manufacturing of bridging materials, there is a wide variation in their structural durability in operation. For example, particle angularity, morphology, raw material quality, internal damage to the fabric and structures of the bridging materials play an important role in the overall behavior of the materials when subject to forces in the downhole environment. Also, there are variations in the sources of physical, chemical, mechanical, and geological characteristics; degree of purity; and level of compliance with manufacturer's quality assurance measures among bridging materials. Because of the wide variation in the mechanical durability of bridging materials in downhole conditions, the identification and selection of highly durable bridging materials is critical in formulating drilling fluids to minimize formation damage while drilling.

One prior art process for quality control and quality assurance of sized bridging materials used in drill-in fluid formulation is disclosed in Applicant's co-pending U.S. patent application Ser. No. 12/897,910, filed Oct. 5, 2010. That process provides suitable quality control and quality assurance for coarse and medium sized bridging materials. Another prior art process for quality control and quality assurance of sized bridging materials used in drill-in fluid formulation is disclosed in Applicant's co-pending U.S. Patent Application No. 61/542,606, filed Oct. 3, 2011, entitled "Improved and Automated Method for Quality Control and Quality Assurance of Sized Bridging Material,". That process provides suitable quality control and quality assurance for all sized bridging materials. The process accomplishes this by developing a metric that quantifies the relative strength of the sized bridging materials. Neither process provides a classification system that includes a comprehensive ranking of sized bridging materials. In addition, neither process provides a classification system that gives an empirical context to mud technicians, mud engineers, mud chemists, drilling engineers, and mud consultants to understand and interpret strength or toughness differences between sized bridging materials to select the appropriate sized bridging material mixtures. Therefore, a classification system is needed that will allow for comparison and selection of sized bridging materials by persons throughout the development, production, and operational processes involving sized bridging materials.

SUMMARY OF THE INVENTION

These and other problems are generally solved or circumvented, and technical advantages are generally achieved, by preferred embodiments of the present invention that provide a sized bridging materials classification scheme for superior drill-in fluid design.

In accordance with an embodiment of the present invention, a method for selecting sized bridging materials for use in drill-in fluid is disclosed. The method identifies a durability metric for sized bridging materials that represents a relative strength of the sized bridging materials. Then the method identifies a value range of the durability metric that correlates to a higher relative strength and a value range of the durability metric that correlates to a lower relative strength. Then the method tests a sample of sized bridging materials to determine the durability metric for the sample, and in the event that the durability metric for the sample is within the value range of the higher relative strength, the method selects the sized bridging material for use in drill-in fluid.

In accordance with another embodiment of the present invention, a method for identifying a relative strength of sized bridging materials for use in drill-in fluid is disclosed. The method tests a size bridging material to determine an absolute value of a D50 shift factor. The method then compares the D50 shift factor for the sized bridging material to a set of rules in a rule base, the rules corresponding to a relative strength of the sized bridging material for use in drill-in fluid. When a match is found between the particular one of the set of rules in the rule base, the method determines a relative strength for the tested sized bridging material that correlates to the rule in the rule base. The method then associates the test sized bridging material with the relative strength correlating to the rule in the rule base.

In accordance with yet another embodiment of the present invention, a method for identifying a relative strength of sized bridging materials for use in drill-in fluid is disclosed. The method tests a size bridging material to determine an absolute value of a D50 shift factor. The method then compares the D50 shift factor for the sized bridging material to a set of rules in a rule base, the rules corresponding to a relative strength of the sized bridging material for use in drill-in fluid. When a match is found between the particular one of the set of rules in the rule base, the method determines a relative strength for the tested sized bridging material that correlates to the rule in the rule base. The method then associates the test sized bridging material with the relative strength correlating to the rule in the rule base. The method then assigns a classification rating to the batch of sized bridging materials from which the sample was selected.

An advantage of a preferred embodiment is that it provides a classification scheme that may be used as a reliable tool to assess the quality of all sized bridging materials available for drilling, drill-in, and completion fluid design. In addition, the disclosed classification scheme provides a comprehensive ranking of sized bridging materials that gives a meaningful context for selection and use of sized bridging materials by mud technicians, mud engineers, mud chemists, drilling engineers, mud consultants, and the like.

BRIEF DESCRIPTION OF THE DRAWINGS

So that the manner in which the features, advantages and objects of the invention, as well as others which will become apparent, are attained, and can be understood in more detail, more particular description of the invention briefly summarized above may be had by reference to the embodiments thereof which are illustrated in the appended drawings that form a part of this specification. It is to be noted, however, that the drawings illustrate only a preferred embodiment of the invention and are therefore not to be considered limiting of its scope as the invention may admit to other equally effective embodiments.

FIG. 2A is schematic showing an oblique transparency view of an apparatus and two axes of rotation therein according to an embodiment of the present invention.

FIG. 2B is a schematic showing a radial cutaway of an apparatus according to an embodiment of the present invention.

FIG. 3A is a schematic drawing of an oblique view of an apparatus according to an embodiment of the present invention.

FIG. 3B is a schematic showing a radial cutaway of an apparatus according to an embodiment of the present invention.

FIG. 3C is a schematic drawing of an oblique view of an apparatus according to an embodiment of the present invention.

FIG. 9 is a classification table illustrating a classification system in accordance with an embodiment of the present invention.

DETAILED DESCRIPTION OF THE PREFERRED EMBODIMENT

Figure 1A:
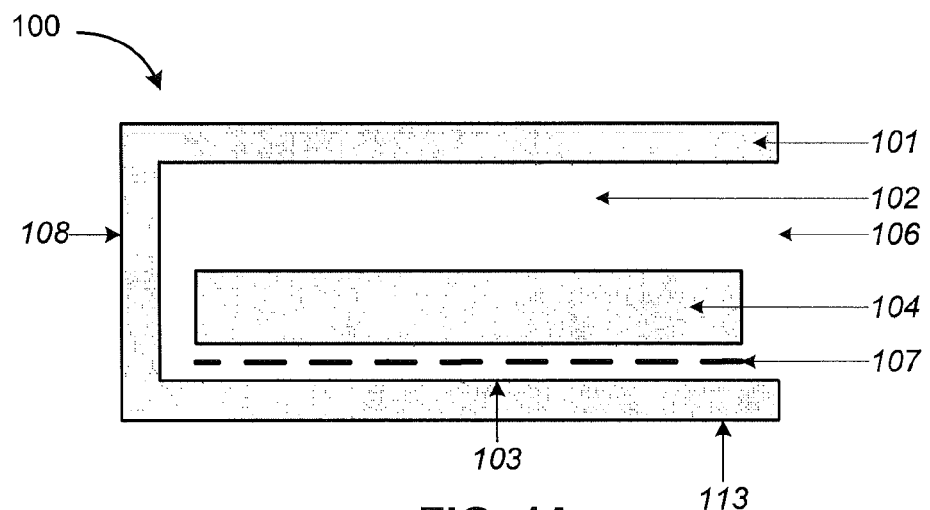
FIG. 1A is a schematic showing an axial cutaway of an apparatus according to an embodiment of the present invention.

The present invention will now be described more fully hereinafter with reference to the accompanying drawings which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout, and the prime notation, if used, indicates similar elements in alternative embodiments.

In the following discussion, numerous specific details are set forth to provide a thorough understanding of the present invention. However, it will be obvious to those skilled in the art that the present invention may be practiced without such specific details. Additionally, for the most part, details concerning sized bridging material selection, drill-in fluid use, drill-in fluid circulation, and the like have been omitted inasmuch as such details are not considered necessary to obtain a complete understanding of the present invention, and are considered to be within the skills of persons skilled in the relevant art.

This application is related to co-pending U.S. patent application Ser. No. 12/897,910, filed Oct. 5, 2010, entitled "Method and Apparatus for Quality Control and Quality Assurance of Sized Bridging Materials Used in Drill-In Fluid Formulation," the disclosure of which is incorporated herein by reference. This application is related to co-pending U.S. Provisional Patent Application No. 61/542,606, filed Oct. 3, 2011, entitled "Improved and Automated Method for Quality Control and Quality Assurance of Sized Bridging Material," the disclosure of which is incorporated herein by reference.

Embodiments of the present invention include an apparatus for testing structural durability characteristics of sized bridging materials by simulating downhole tool interactions and wet grinding actions upon sized bridging materials. The apparatus 100 can be shown with reference to FIG. 1A, FIG. 1B, FIG. 2A, and FIG. 2B. The apparatus 100 includes a cylindrical tubular container 101 having an outer surface 113 that is substantially cylindrically shaped. As can be shown with reference to the cross-section of FIG. 1A, the tubular container 101 is hollow, and the open space within the tubular container 101 is bound by an inner surface 103 of the tubular container. The inner space of the tubular container 101 is also of a substantially cylindrical shape, and is defined herein as a testing cell 102.

The tubular container 101 also has two ends 108 and 106 that correspond to bases of the cylindrical shape of the tubular container 101. A major axis 111 of the tubular container 101, as can be shown with respect to FIG. 1B, corresponds to the axis of the cylinder represented by the substantially cylindrical shape of the tubular container 101, and the major axis 111 intersects the centers of the bases of the cylindrical shape of the tubular container 101, as is shown in FIG. 1B. The end 108 of the tubular container 101 can be, for example, a closed end having a sealing cap positioned thereon in any suitable manner. A person skilled in the art will understand that the sealing cap can be permanently or non-permanently attached to the end 108 or integrally joined with the tubular container 101 to close the end 108 of the tubular container 101. The sealing cap may be, for example, screwed, pressed, or otherwise permanently or non-permanently attached to the tubular container 101 at the end 108. The end 106 of the tubular container 101 can be, for example, an open end or a closed end having a removable sealing lid 109, as can be shown with respect to FIG. 2A. The removable sealing lid 109 can be screwed onto or positioned thereon in any manner known to those skilled in the art so that the sealing cap can be non-permanently attached to the tubular container 101 to close the end 106 of the tubular container 101. The sealing lid 109 may be, for example, screwed, pressed, or otherwise non-permanently attached to the tubular container 101. As can be shown in FIG. 1A, the testing cell 102 can be physically accessible at the end 106 of the tubular container 101 when the removable sealing lid 109 is removed.

As can be shown with respect to FIG. 2A, the apparatus 100 also includes a roller 105 to rotate the tubular container 101. The roller 105 can positioned to apply force to the tubular container 101 so that the tubular container 101 rotates about its major axis 111. In one embodiment, the roller 105 rotates in a counterclockwise direction 154 about an axle 156. The roller 105 is in physical contact with the outer surface 113 of the tubular container 101 while the major axis 111 of the tubular container 101 is positioned horizontal and substantially parallel to the axle 156 of the roller 105. A person skilled in the art will understand that roller 105 may also rotate in a clockwise direction. As can be shown with respect to FIG. 2B, the rotation in the counterclockwise direction 154 of the roller 105 while in physical contact with the outer wall of the tubular container 101 causes the roller 105 to apply a force 153 to the outer surface 113 of the tubular container 101. The applied rotation causes the tubular container 101 to rotate in a clockwise direction 155 about its major axis 111. A person skilled in the art will understand that in the event that the roller 105 rotates in a clockwise direction, tubular container 101 may rotate in a counterclockwise direction. A person skilled in the art will further understand that various measures may be employed to stabilize the roller 105 and the tubular container 101 so that the roller 105 and the tubular container 101 remain in physical contact while the tubular container 101 rotates about its major axis 111. For example, as illustrated in FIG. 3A and FIG. 3B, the tubular container 101 can be positioned horizontally upon on several rollers 151 so that the tubular container 101 is entirely supported by the rollers 151 while the tubular container 101 rotates about its major axis 111. Axles 156 for the rollers 151 can be positioned in a fixed structure 152, for example, using bushings to allow rotation of the axles 156 within the fixed structure 152. The roller 105 can be driven by an electric motor 351, as can be shown with respect to FIG. 4, according to drive configurations known to those having skill in the art. The electric motor 351 can also be attached to a fixed structure 152, and the motor 351 can provide a torque to the axles 156, for example, to rotate the roller 105, causing the tubular container 101 to rotate about its major axis 111. The rotational speed for rotating the roller 105, as is described further herein, shall be sufficient to allow simulated downhole tool interactions within the tubular container 101 but shall not exceed a speed that allows the tubular container 101 to remain positioned on the rollers 151 during rotation.

Figure 1B:
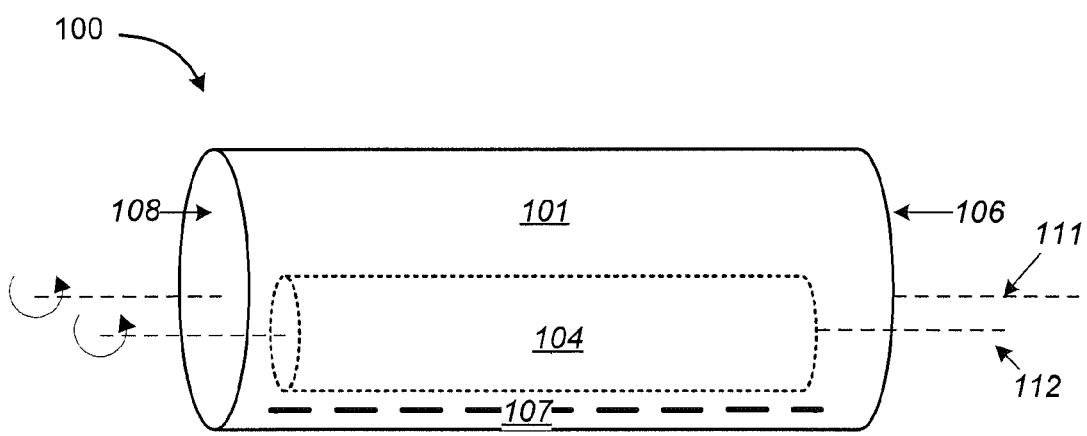
FIG. 1B is schematic showing a transparency view of an apparatus and two axes of rotation therein according to an embodiment of the present invention.

As can be shown with reference to FIG. 1A, FIG. 1B, FIG. 2A, and FIG. 2B, the apparatus 100 further includes a loose cylindrical rod 104 positioned in the testing cell 102. The loose cylindrical rod 104 is supported within the testing cell 102 by a tubular wall of the tubular container 101 when the loose cylindrical rod 104 rests along the lowest portion of the cylindrical inner surface 103 of the testing cell 102. Because the loose cylindrical rod 104 is loose, it can roll freely along the cylindrical inner surface 103 of the testing cell 102 when the tubular container 101 rotates about its major axis 111, as has been described herein. The position of the loose cylindrical rod 104 in the testing cell 102, as is shown in FIG. 2B, can remain substantially near the bottom of the testing cell 102 during the rotation of the tubular container 101. A major axis 112 of the loose cylindrical rod 104, as can be shown with respect to FIG. 1B, corresponds to the axis of the cylindrical shape of the loose cylindrical rod 104, and the major axis 112 intersects the centers of the bases of the cylindrical shape of the loose cylindrical rod 104. As is shown in FIG. 1A and FIG. 1B, the loose cylindrical rod 104 can be positioned in the testing cell 102 so that the major axis 112 is substantially parallel to the major axis 111 of the tubular container 101. For example, loose cylindrical rod 104 and testing cell 102 are positioned horizontally in FIG. 1A and FIG. 1B and the loose cylindrical rod 104 is positioned on the cylindrical inner surface 103 of the testing cell 102.

As can be shown with reference to FIG. 2A, the apparatus 100 can further include a sealing lid 109 positioned on the tubular container 101 to cover the open end 106 of the tubular container 101. The sealing lid 109 can be a removable unit or assembly that can be attached to the tubular container 101 at the open end 106 of the tubular container 101 to enclose and seal the contents of the testing cell 102, including the loose cylindrical rod 104 and any other contents placed therein, such as sized bridging materials 107 and liquid. The sealing lid 109 can be attached to the tubular container 101 as will be appreciated by those skilled in the art, including using a threaded screw-on attachment wherein the tubular container 101 and the sealing lid 109 have compatible threads. In certain embodiments, the removable sealing lid 109 can include a relief valve 110 to vent high pressures within tubular container 101. High pressures may occur when testing is performed under high temperatures to simulate borehole conditions. The relief valve can be, for example, a stem valve manufactured by OFI Testing Equipment, Inc. of Houston, Tex.

The apparatus 100 can have preselected dimensions within a range of dimensions to allow or enhance a bench-sized simulation of downhole tool interactions and wet grinding actions of a borehole environment within the testing cell 102. The dimensions of the testing cell 102 and the loose cylindrical rod 104, for example, can be preselected to enhance the simulation of downhole tool interactions and wet grinding actions of a borehole environment upon a sample of sized bridging materials 107 positioned within the testing cell 102, as is shown in FIG. 1A, FIG. 1B, FIG. 2A, and FIG. 2B. For example, the testing cell 102 can have a volume of 400 cubic centimeters (cc) or greater, a mass in the range of 3,200 to 3,300 grams, a length in the range of 7.0 to 8.0 inches, and a diameter in the range of 2.25 to 2.75 inches. Also, for example, the loose cylindrical rod 104 can be cut or milled of solid steel and have a mass in the range of 550 to 600 grams, a length of 6.0 to 6.25 inches, and an outer diameter in the range of 1.0 to 1.5 inches. In the example, the sealing lid 109 may have a height in the range of 0.5 to 0.75 inches, a diameter of 3.00 to 3.25 inches, and a mass of 575 to 600 grams; the relief valve 110 can have a length of 1.75 to 2.00 inches, a diameter of 0.25 to 0.50 inches, and a mass of 15 to 20 grams.

Figure 4:
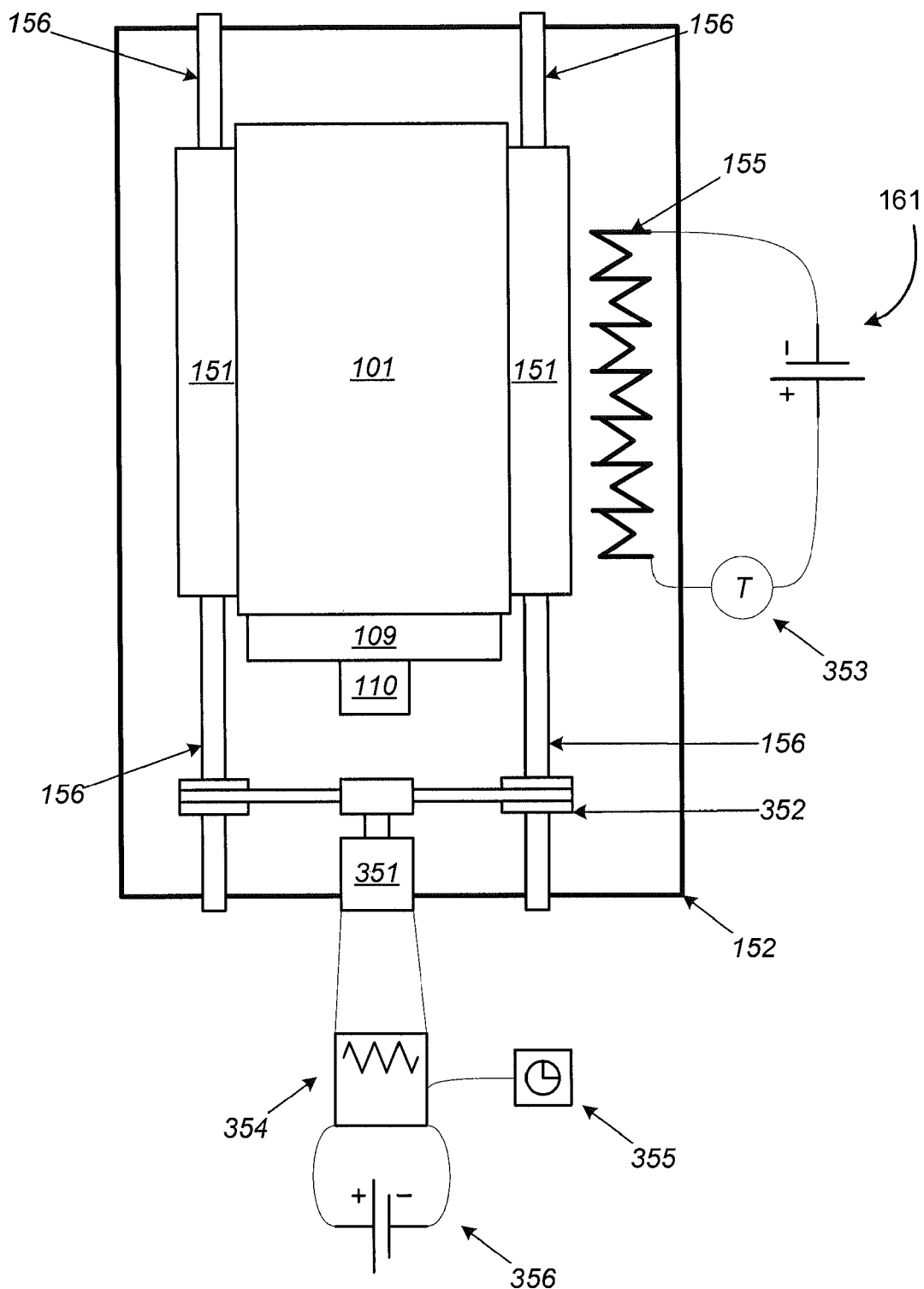
FIG. 4 is a schematic showing of a top or layout view of an apparatus according to an embodiment of the present invention.

The apparatus 100 can further include a temperature-controlled rolling environment 161 as can be shown with reference to FIG. 3C and FIG. 4. The temperature-controlled rolling environment 161 can include an insulated shell 157, for example, that attaches to the fixed structure 152 so as to enclose the tubular container 101 and maintain a preselected temperature to enhance the simulation of downhole tool interactions and wet grinding actions of a borehole environment upon a sample of sized bridging materials 107 positioned within the testing cell 102. The temperature-controlled rolling environment 161 can include, for example, an insulated shell 157, a heating element 155 inside the insulated shell 157, and a thermostat 353 to control the temperature of the heating element 155. Insulated shell 157 can be constructed, for example, using stainless steel. The insulated shell 157 can include, for example, insulated gasket 159 between the insulated shell 157 and the fixed structure 152. In one embodiment, as illustrated in FIG. 3C, the heating element 155, for example, can include an electric heating coil positioned within the insulated shell 157 and capable of heating the tubular container 101 by convection. In other embodiments, the heating element 155, for example, can include heating coils positioned within the roller 151 that are capable of heating the tubular container 101 by conduction. The thermostat 353, as will be appreciated by those having skill in the art, can be set to a preselected temperature, for example, by a human operator, and control the temperature of the tubular container 101 or the testing cell 102 by adjusting the output of the heating coil 155 so that the preselected temperature is achieved. Thermostat 353 can be, for example, an electronic solid state thermostat manufactured or provided by OFI Testing Equipment, Inc. of Houston, Tex.

The apparatus 100 can further include a speed controller 354 and a timer 355 to drive the motor 351 at a preselected speed for a preselected time. The motor 351 can be, for example, any sort of alternating current (AC), direct current (DC), or universal electric motor driven by an electrical current source 356. The speed controller 354 can be any sort of electric or mechanical speed controller, such as a thyristor circuit, for example, as will be known to those having skill in the art.

Those of skill in the art will appreciate that the motor 351 and the speed controller 354 can be selected to rotate tubular container 101 at a speed in the range of 25 to 35 revolutions per minute, as such rotational speed is desirable for effectively simulating grinding actions within the testing cell 102. The motor 351 can be, for example, an electric motor model "174-13" manufactured or provided by OFI Testing Equipment, Inc. of Houston, Tex. The speed controller 354 can be, for example, controller model "174-14" manufactured or provided by OFI Testing Equipment, Inc. of Houston, Tex.

Figure 5:
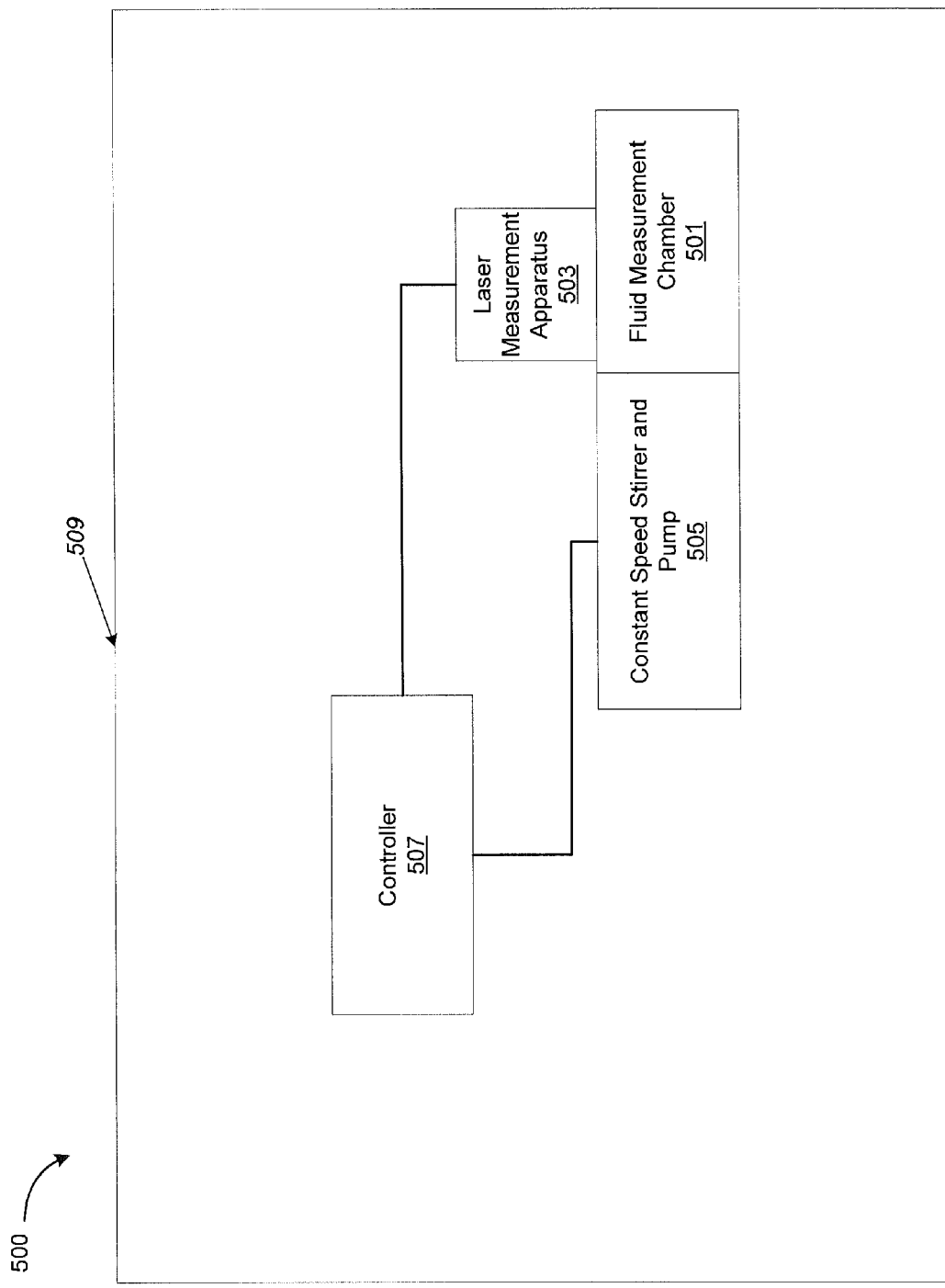
FIG. 5 is a schematic representation of a laser particle size analyzer in accordance with an embodiment of the present invention.

Embodiments of the disclosed invention may also include a laser particle size analyzer 500 as shown in FIG. 5. Laser particle size analyzer 500 may include a fluid measurement chamber 501, a laser measurement apparatus 503, a constant speed stirrer and pump 505, and a controller 507 all mounted within a frame assembly 509. A person skilled in the art will understand that frame assembly 509 may be any suitable assembly such that laser particle size analyzer 500 may operate as described below. Frame assembly 509 may be a single self contained unit allowing laser particle size analyzer 500 to operate as a single unit. Frame assembly 509 and laser particle size analyzer 500 may also comprise multiple units operationally coupled to operate as described below.

Fluid measurement chamber 501 may be a fluid chamber having a volumetric capacity less than or equal to the tubular container 101 (FIG. 1) so that all or a portion of the fluid in tubular container 101 may be transferred from tubular container 101 to fluid measurement chamber 501. Fluid measurement chamber 501 will have a shape and opacity such that laser measurement apparatus 503 may be in optical communication with fluid in fluid measurement chamber 501 during particle size measurement. Constant speed stirrer or pump 505 is in communication with fluid measurement chamber 501 to circulate or mix fluid contained in fluid measurement chamber 501 during a particle size test, described in more detail below. Controller 507 may be an integral unit to laser particle size analyzer 500 or, alternatively, a separate unit. Controller 507 may be communicatively coupled to laser measurement apparatus 503 and pump 505. Controller 507 may include software adapted to operate laser measurement apparatus 503 for particle size measurement using a controlled repeatable process that limits user variability to increase data reliability. Controller 507 may also conduct automatic data recording operations that may be stored in any suitable storage medium and displayed on any suitable display medium. In an embodiment, laser particle size analyzer 500 will include a display for presentation of the particle size analysis described in more detail below. In an another embodiment, laser particle size analyzer 500 will be communicatively coupled to a personal computing device having a display for presentation of the particle size analysis. Laser particle size analyzer 500 may be, for example, a "Mastersizer 2000" model or an "Insitec" model manufactured or provided by Malvern Instruments, Ltd.

During particle size analysis, controller 507 will operate laser measurement apparatus 503 to direct a laser beam through a solution within fluid measurement chamber 501. Pump 503 will operate to circulate the solution within fluid measurement chamber 501 to prevent separation of the suspended particles from the fluid. The suspended particles in the solution contained within fluid measurement chamber 501 will diffract the light from the laser beam of laser measurement apparatus 503. The diffracted light may be focused onto a detector of the laser measurement apparatus 503. The detector of laser measurement apparatus 503 will measure the angular distribution of the intensity of the scattered light. The measured intensity of the angular distribution of the scattered light may be correlated to a size of the particles in the suspension within fluid measurement chamber 501. This is done according to the theory of Fraunhofer diffraction that states that the intensity of light scattered by a particle is directly proportional to the size of the particle.

Embodiments of the present invention also include methods for testing the hardness-related structural durability characteristics of sized bridging materials by simulating downhole tool interactions and wet grinding actions upon sized bridging materials. The methods can be shown with reference to FIG. 2A, FIG. 6, FIG. 7A, FIG. 7B, and FIG. 7C.

Testing samples for the method disclosed herein may be selected from a bulk of sized bridging materials that are considered to be of the same grade, i.e. fine, medium, or coarse sized bridging materials. As used herein, materials of the same grade generally mean one of the four grades commonly used by the oil and gas industry. For example, sized bridging materials having a mass median diameter or D50 value of 2 to 5 microns are considered ultra-fine grade, sized bridging materials having a mass median diameter or D50 value of 10 to 14 microns are considered fine grade, sized bridging materials having a mass median diameter or D50 value of 135 to 165 microns are considered medium grade, and sized bridging materials having a mass median diameter or D50 value of 550 to 650 microns are considered coarse grade. A person skilled in the art will understand that other grades of sized bridging material may be used and classified in accordance with the disclosed embodiments.

The bulk of sized bridging materials can be, for example, from a mass of approximately 2 kilograms in total. The bulk of sized bridging materials can include solid particles, typically composed of calcium carbonate (CaCO3), dolomite, or marble, which are designed to "bridge" across the pore throat or fractures in reservoir rock when formulated in a drill-in fluid and used in oil and gas drilling operations. In the illustrated embodiment, the test samples may include a solids portion and a fluid portion. The solids portion and the fluid portion may be mixed prior to testing or, alternatively, mixed during the testing process. Any resulting suspension of solids portion and fluid portion, which may be referred to as a "mud," can be tailored to specific geological applications by employing a tailored range of the bridging material sizes to achieve a desired fluid density and bridging ability. Bridging materials can be manufactured to certain sizes such as coarse, medium, fine, or very fine, which allows the selection of a particular size distribution scheme corresponding to the pore throat sizes of a target reservoir.

Figure 6:
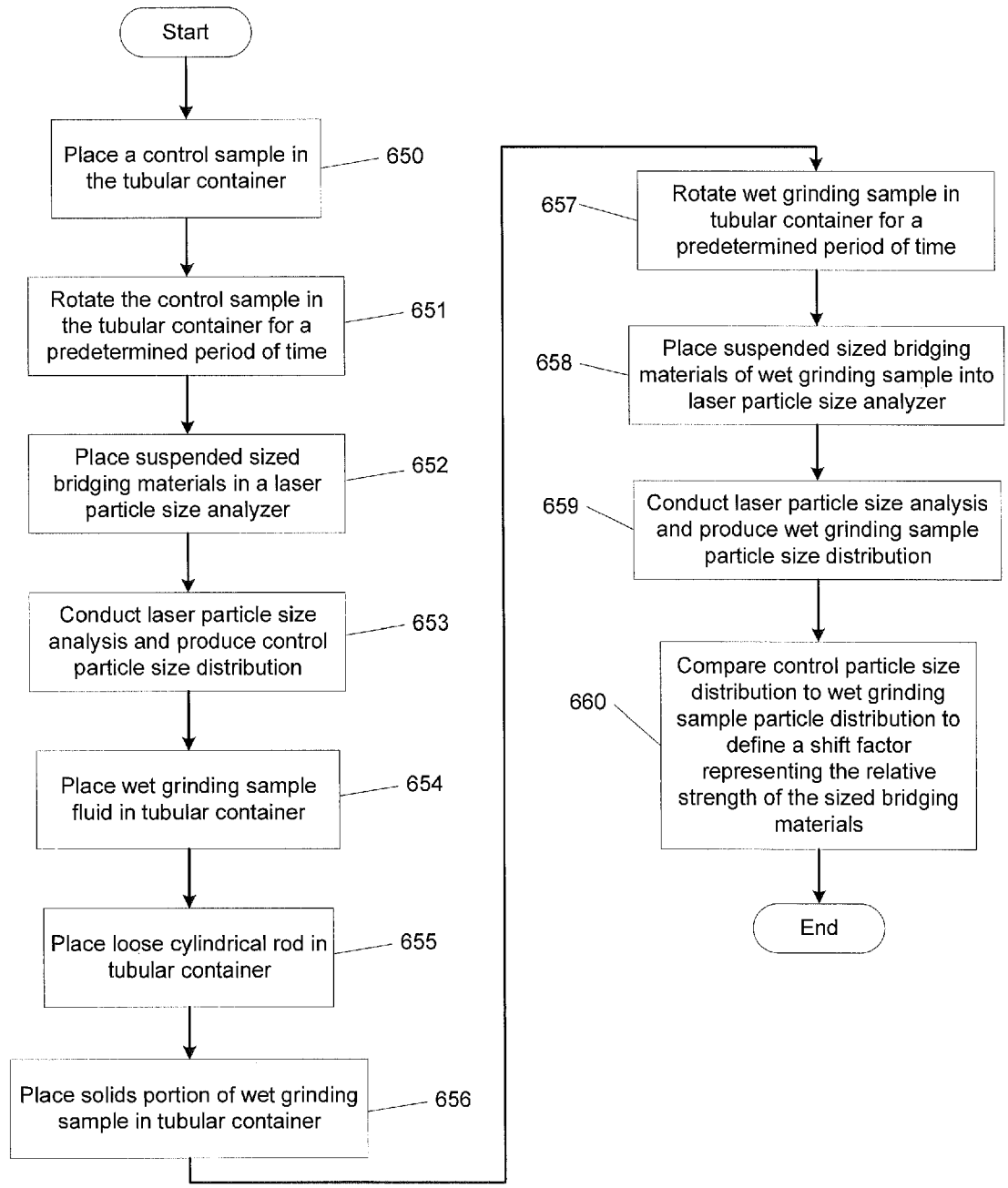
FIG. 6 is a flow chart illustrating operational steps in accordance with an embodiment of the present invention.

Referring to FIG. 6, embodiments of methods according to the present invention include placing a control sample into tubular container 101 as shown at 650. The control sample may include a preselected mass sample of sized bridging materials suspended in a test volume of fluid. For example, a 25 gram sample of sized bridging materials may be placed into tubular container 101 with a 350 ml volume of water. As shown at 651, the control sample may then be rotated for a predetermined period of time. For example, after securing tubular container 101 with sealing lid 109 and closing relief valve 110, tubular container 101 may be rotated by roller 105 for a period of 2 hours. A person skilled in the art will understand that rotation may occur at the ambient temperature of the testing environment or alternatively at a temperature that simulates the expected borehole temperature. A person skilled in the art will further understand that if rolling is conducted at the simulated borehole temperature, the control sample will be allowed to return to the temperature of the ambient testing environment prior to further testing operations. Loose cylindrical rod 104 may not be placed within tubular container 101 at this time. After restoring a pressure balance to the interior of tubular container 101 through relief valve 110, a volumetric sample of the material within tubular container 101 containing both sized bridging materials and the fluid in which the sized bridging materials are suspended will be removed from tubular container 101 and placed within fluid measurement chamber 501 of laser particle size analyzer 500 as shown at 652. Laser particle size analyzer 500 will conduct a particle size test to determine a control particle size distribution for the control sample as shown at 653. The control particle size distribution will produce values representing the range of particle sizes in the control sample. One of the produced values may be the D50 or mass median diameter value. The D50 value may be considered the average particle diameter by mass of the log-normal distribution of the particle sizes. Thus, the control particle size distribution will produce a D5 control value.

Tubular container 101 may then be cleaned to remove any remaining material of the control sample from tubular container 101 or, alternatively, not. At 654, a fluid portion of a wet grinded sample may then be placed into tubular container 101. The fluid portion may be any suitable volume of any suitable fluid. For example, the fluid portion of the wet grinded sample may be 350 ml of water. A person skilled in the art will recognize that the type of fluid and fluid volume used in both the control test and the wet grinded test should be equivalent volumes of the same type of fluid to ensure reliability of the testing method. However, because measurements are taken of the particle size distribution and not of the particle mass, it is not necessary to strictly ensure that the fluid and solids portions of the control and wet grinding samples are exactly the same. Following placement of the fluid portion of the wet grinded sample into tubular container 101, at 655, loose cylindrical rod 104 may be placed into tubular container 101. The solids portion of the wet grinded sample, i.e. the sized bridging materials, may then be placed within tubular container 101 as shown at 656. For example, a 25 gram sample may be placed into tubular container 101. A person skilled in the art will recognize that the solids portion sample size should have an equivalent mass to the solids portion of the control sample and be selected from the same larger bulk of sized bridging materials. A person skilled in the art will also recognize that a more reliable measurement of the strength of the sized bridging materials is achieved by placing the solids portion of the wet grinding sample into tubular container 101 after placing loose cylindrical rod 104 into tubular container 101. Placing the materials into tubular container 101 in this manner will limit impact damage to the solids portion sample that are not the result of the testing method. While the testing method may be carried out without placing the materials into tubular container 101 in this order, the resultant test may not accurately reflect the relative strength of the sized bridging materials.

At 657, the wet grinding sample may then be rotated for a predetermined period of time. For example, after securing tubular container 101 with sealing lid 109 and closing relief valve 110, tubular container 101 may be rotated by roller 105 for a period of 2 hours. A person skilled in the art will understand that rotation may occur at the ambient temperature of the testing environment or alternatively at a temperature that simulates the expected borehole temperature. A person skilled in the art will further understand that if rotation is conducted at the simulated borehole temperature, the wet grinding sample will be allowed to return to the temperature of the ambient testing environment prior to further testing operations. A person skilled in the art will also understand that in the event the control sample is heated during rotation at 651, the wet grinding sample may be heated at rotation at 657 to increase results reliability. After restoring a pressure balance to the interior of tubular container 101 through relief valve 110, a volumetric sample of the material within tubular container 101 containing both sized bridging materials and the fluid in which it is suspended will be removed from tubular container 101 and placed within fluid measurement chamber 501 of laser particle size analyzer 500 as shown at 658. Laser particle size analyzer 500 will conduct a particle size test at 659 to determine a particle size distribution for the wet grinding sample. The particle size distribution will include a D50 value for the wet grinding sample.

Once the particle size distributions for the control sample and the wet grinding sample have been determined, the particle size distributions may be compared at 660 to determine a relative strength of the tested sized bridging materials. For example, in the illustrated embodiment, the D50 wet grinding value may be subtracted from the D50 control value to determine the difference in the D50 mass median diameter of the particles in each sample. The D50 difference may then be divided by the D50 control value to determine a D50 shift factor. The D50 shift factor is a ratio of the difference in the D50 mass median diameter between the control and wet grinding samples to the D50 value for the control sample. The D50 Shift factor provides a means to compare relative strengths of sized bridging materials for selection of an appropriate sized bridging material for use in a wellbore as described in more detail below.

Use of loose cylindrical rod 104 at 655 simulates downhole tool interactions upon the wet grinding sample so that the effects of the downhole tool interactions upon the selected sized bridging materials may be measured. Embodiments of methods according to the present invention can, for example, simulate bit grinding effects, bit nozzle impact, mud motor impact, and hydrodynamic shearing action of downhole fluids, tools, and equipment.

Figure 7A:
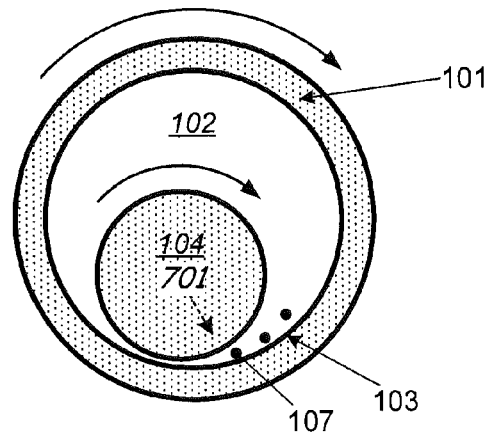
FIG. 7A is a schematic drawing showing methods according to an embodiment of the present invention.
Figure 7B:
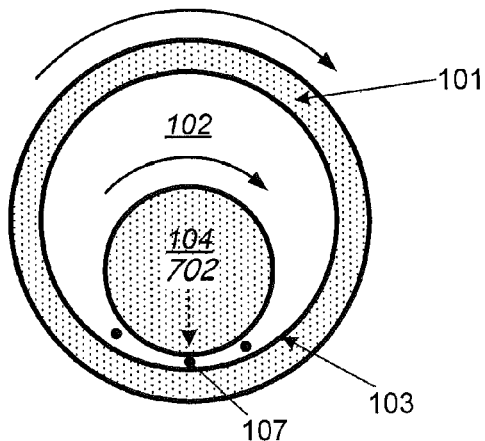
FIG. 7B is a schematic drawing showing methods according to an embodiment of the present invention.
Figure 7C:
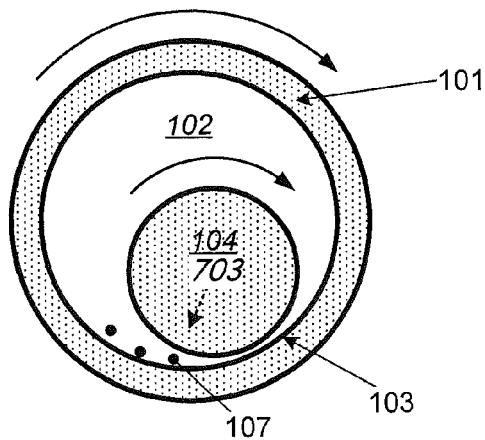
FIG. 7C is a schematic drawing showing methods according to an embodiment of the present invention.

Rotating the wet grinding sample with loose cylindrical rod 104 at 657 simulates downhole tool interactions upon the test sample by rolling the loose cylindrical rod 104 in relation to the cylindrical inner surface 103 of the testing cell 102 as can be shown with respect to FIG. 7A, FIG. 7B, and FIG. 7C. When the loose cylindrical rod 104 rolls in relation to the bottom portion of the cylindrical inner wall 103 of the testing cell, the loose cylindrical rod 104 applies a force to the plurality of sized bridging materials in the wet grinding sample, i.e., a crushing force between the loose cylindrical rod 104 and the cylindrical inner surface 103 of the testing cell 102, such that the wet grinding sample is partially crushed. The forces applied to the wet grinding sample between the freely loose cylindrical rod 104 and the cylindrical inner surface 103 of the testing cell 102 are able to simulate downhole tool interactions upon the wet grinding sample, specifically wet grinding action. A freely rolling loose cylindrical rod 104 that can roll along the bottom portion of the cylindrical inner wall 103 of a cylindrical testing cell 102 provides an enhanced simulation of downhole tool interactions over other types of actions, for example known methods for completely crushing particles, such the crushing action provided by a piston.

As can be shown with reference to FIGS. 7A, 7B, and 7C, the freely rolling loose cylindrical rod 104 rolls freely with respect to the cylindrical inner surface 103 of the testing cell 102, thereby changing positions with respect to the particles 107 and haphazardly subjecting the particles 107 to forces in multiple directions, for example, directions 701, 702, and 703. Furthermore, the rolling action of the freely rolling loose cylindrical rod 104 can alter the orientation of the particles 107 so that the particles 107 are subject to forces in more than one direction. Because the rolling action of the freely rolling loose cylindrical rod does not have to overcome the resistance of all particles 107 at once, less force can be applied to the particles 107 and the ability to achieve a partial crushing can be enhanced. The ability of the loose cylindrical rod 104 to haphazardly exert forces upon the particles 107 thereby enhances the simulation of downhole tool interactions upon the wet grinding sample. Specifically, the haphazard rolling the loose cylindrical rod 104 freely along the cylindrical inner surface 103 of the cylindrical test cell 102 allows a simulation of the wet grinding process of a borehole environment that causes partial disintegration and dispersion of the bridging materials. The action of rotating the tubular container 101 to rotate the loose cylindrical rod 104 can be performed at a constant preselected rotation speed for a predetermined time period. For example, an effective simulation of the wet grinding action of a borehole environment can be achieved with a rotation speed of 25-35 revolutions per minute (rpm) over a time of 1-4 hours, with a 1 hour duration providing sufficiently discriminatory test results.

When the step of rolling the loose cylindrical rod 104 is complete, the wet grinding sample has been subjected to forces that simulate downhole tool interactions in a manner that causes partial crushing of the wet grinding sample, such as the disintegration and dispersion of participles in the wet grinding sample. It is not the purpose, however, for the wet grinding sample to completely disintegrate; the wet grinding sample may also contain sized bridging materials that were not crushed and maintained their original shape. For example, the wet grinding sample will contain some of the original sized bridging materials. The wet grinding sample may contain both the durable sized bridging materials that were not crushed and the left over of particles that have been crushed. Accordingly, rolling the loose cylindrical rod 104 along the cylindrical inner wall 103 of the testing cell 102 provides a superior simulation of downhole tool interactions in comparison to using a dedicated crushing apparatus, like a piston apparatus, or a grinding apparatus, such as a planetary grinder, which might completely, rather than partially, render granular materials placed therein into a finer particulate matter and would therefore not accurately simulate downhole tool interactions upon the bridging materials.

Embodiments of methods according to the present invention can also include rotating the cylindrical tubular container 101 about its major axis 111 at a preselected rotational speed, for a preselected time period, and while the cylindrical tubular container is maintained at a preselected temperature. The preselected rotational speed, the preselected time period, and the preselected temperature for the rotation can be selected, for example, to best simulate downhole conditions and downhole tool interactions and wet grinding actions. For example, a preselected rotation speed between 25 and 35 revolutions per minute (rpm), a preselected time period of at least one hour, and a preselected temperature in the range of 20-150 degrees Celsius are capable of sufficiently simulating downhole tool conditions and downhole tool interactions and wet grinding actions in a manner that can produce consistent and meaningful test results. The preselected rotational speed, the preselected time period, and the preselected temperature can be enforced or maintained by implementing the structure as described with respect to the temperature-controlled rolling chamber 153, the heating element 155, and the motor 351.

The preselected volume of liquid enclosed in the testing cell 102 in 650 and 654 can be, for example, 350 milliliters of tap water. Tap water, for example, is able to enhance the simulation of the downhole tool interactions, particularly, with respect to an aggressive wet grinding action. Other fluids, such as sea water, salt water, simulated pore fluid, diesel, mineral oil, synthetic oil, esterified oil, or vegetable oils can also be used as the preselected volume of liquid to simulate downhole tool interactions and wet grinding. Any of the foregoing liquids, for example, may be sufficient for simulating downhole tool interactions and wet grinding actions without the addition of chemicals intended to react with a formulation of the bridging materials in the liquid. Embodiments of methods according to the present invention can be used to test the durability of bridging materials for both oil-based and water-based muds.

Embodiments of methods according to the present invention can also include repeating multiple iterations of steps 650-660 as necessary for quality control and quality assurance of sized bridging materials. A number of iterations in the range of 6-7 can provide a statistically significant test, provided that the results are averaged. As can be shown with reference to FIG. 8A-8C, embodiments of methods according to the present invention provide a D50 shift factor value that represents the relative strength of varying sized bridging material samples. In the illustrated embodiments, positive values indicate a reduction of particle size in the testing process through disintegration of particles by the attrition effect, i.e. the wet grinding sample D50 value is less than the control sample D50 value. Negative values indicate an increase in particle size in the testing process through fusion and/or association of particles by the attrition effect, i.e. the wet grinding sample D50 value is greater than the control sample D50 value. Further, smaller absolute values indicate less change in the particle size of the testing samples, while larger absolute values indicate greater change in the particle size of the testing samples.

Figure 8A:
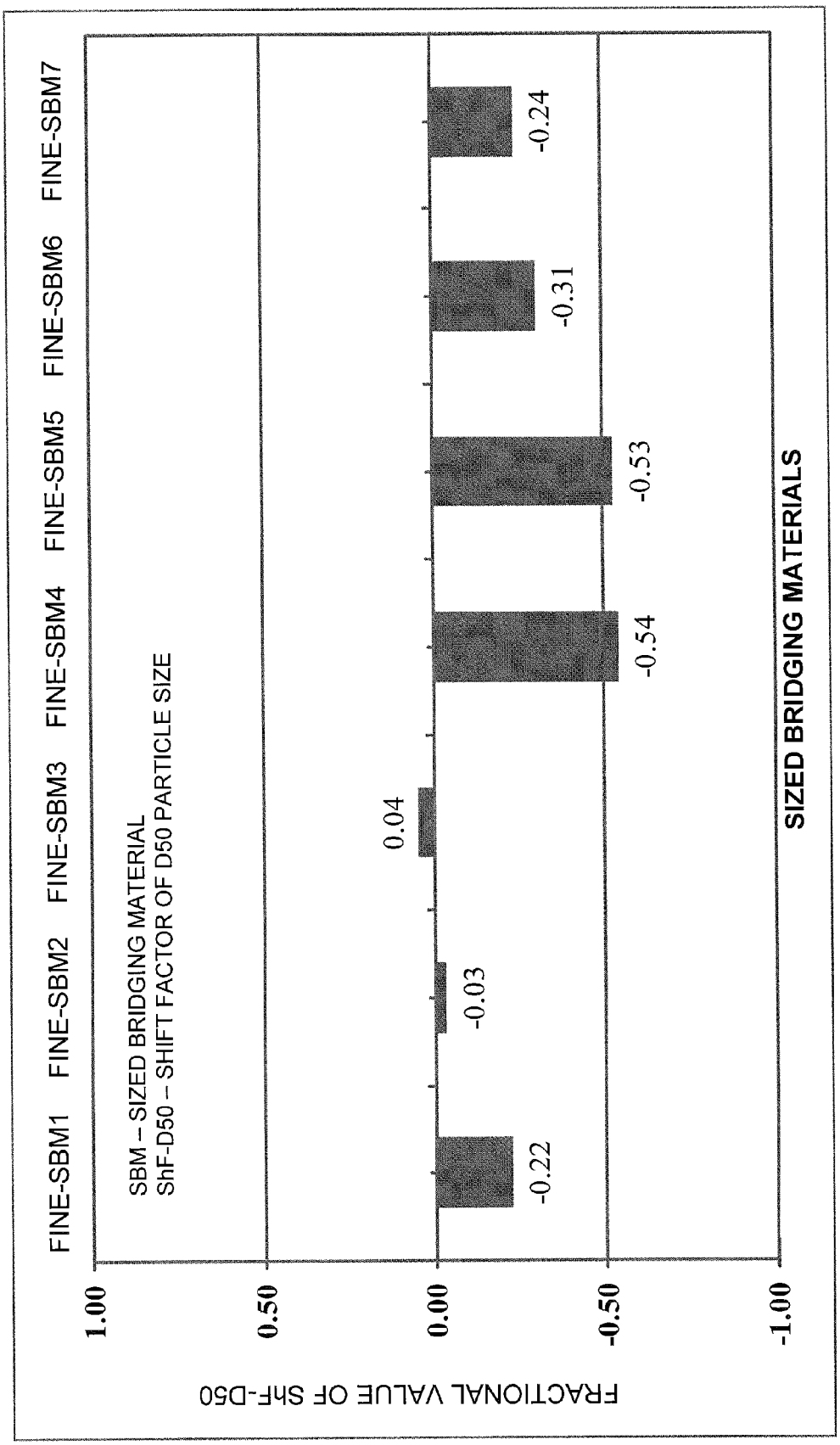
FIGS. 8A-8C are charts showing data produced by embodiments of the present invention, the chart having a fractional shift value on the Y-axis and sized bridging material selection on the X-axis.
Figure 8B:
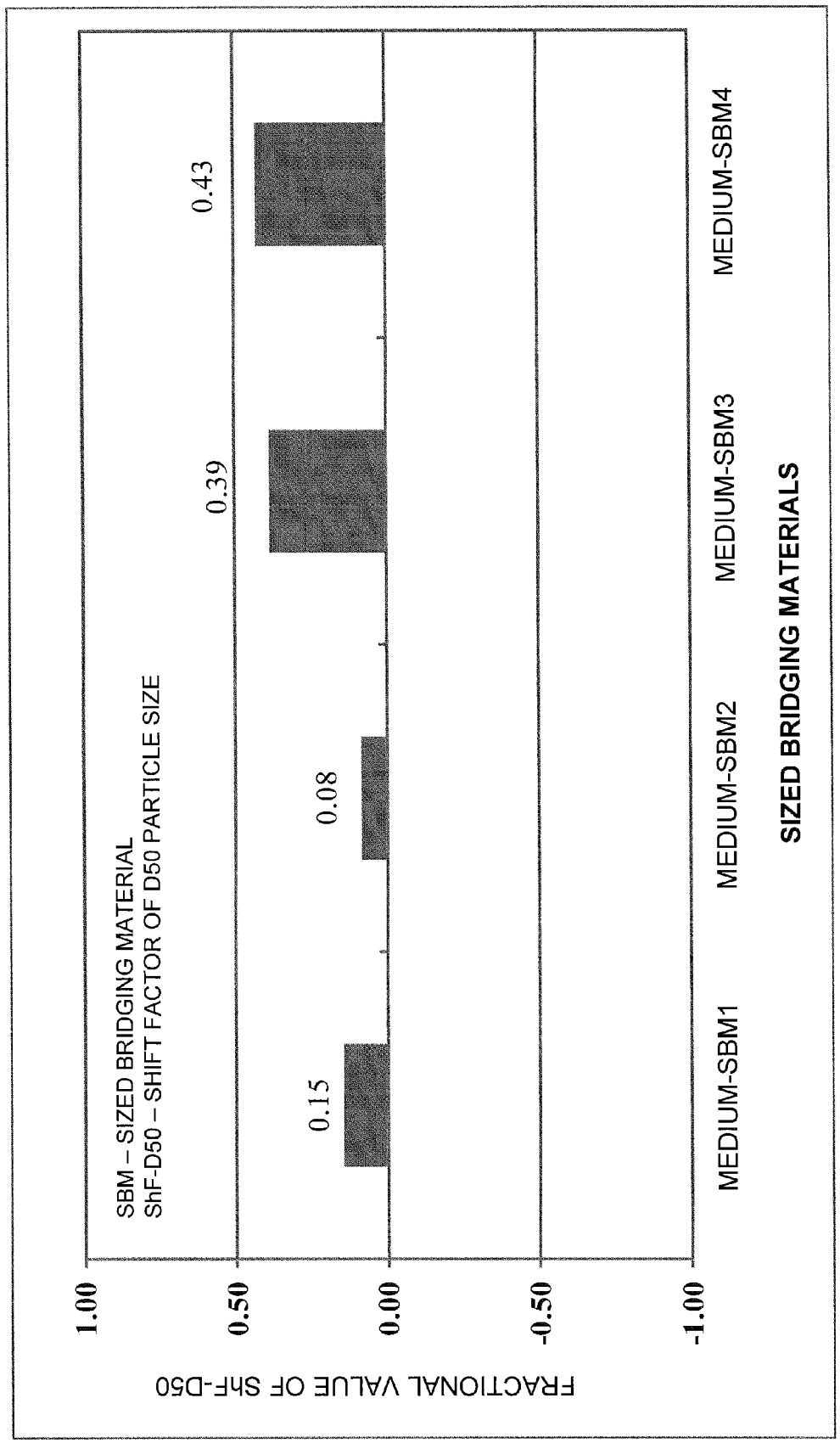

For example, as shown in FIG. 8A, the Fine-SBM2 sample has a small absolute value and a negative sign. This indicates that the Fine-SBM2 sample had little change in particle size and what change occurred resulted in a net increase in particle size. As shown in FIG. 8B, the Medium SBM-2 sample has a small absolute value and a positive sign. This indicates that the Medium-SBM2 sample had little change in particle size and what change occurred resulted in a net decrease in particle size. Both the Fine-SBM2 sample and the Medium-SBM2 sample exhibit high particle strength. Thus, the Fine-SBM2 and Medium-SBM2 sized bridging materials will need infrequent additions of solids material to the drilling mud to maintain the desired particle distribution during wellbore operations because the particle size of the sized bridging materials will not change radically during operating conditions. This reduces mud treatment and management cost. It will also increase drilling efficiency and decrease the scope of formation damage induced by the particles in the drilling mud. This also reduces spurt loss and internal mudcake buildup in the vicinity of the wellbore, aiding the cleaning of the wellbore before completion. The formation of good quality mudcake on the borehole wall will reduce the filtrate loss and cause minimum changes to oil relative permeability in the near wellbore reservoir formation. Thus, pore plugging by fines migration, flow reduction due to relative permeability change, and poro-perm characteristics alteration due to internal mudcake formation will be eliminated or reduced.

Figure 8C:
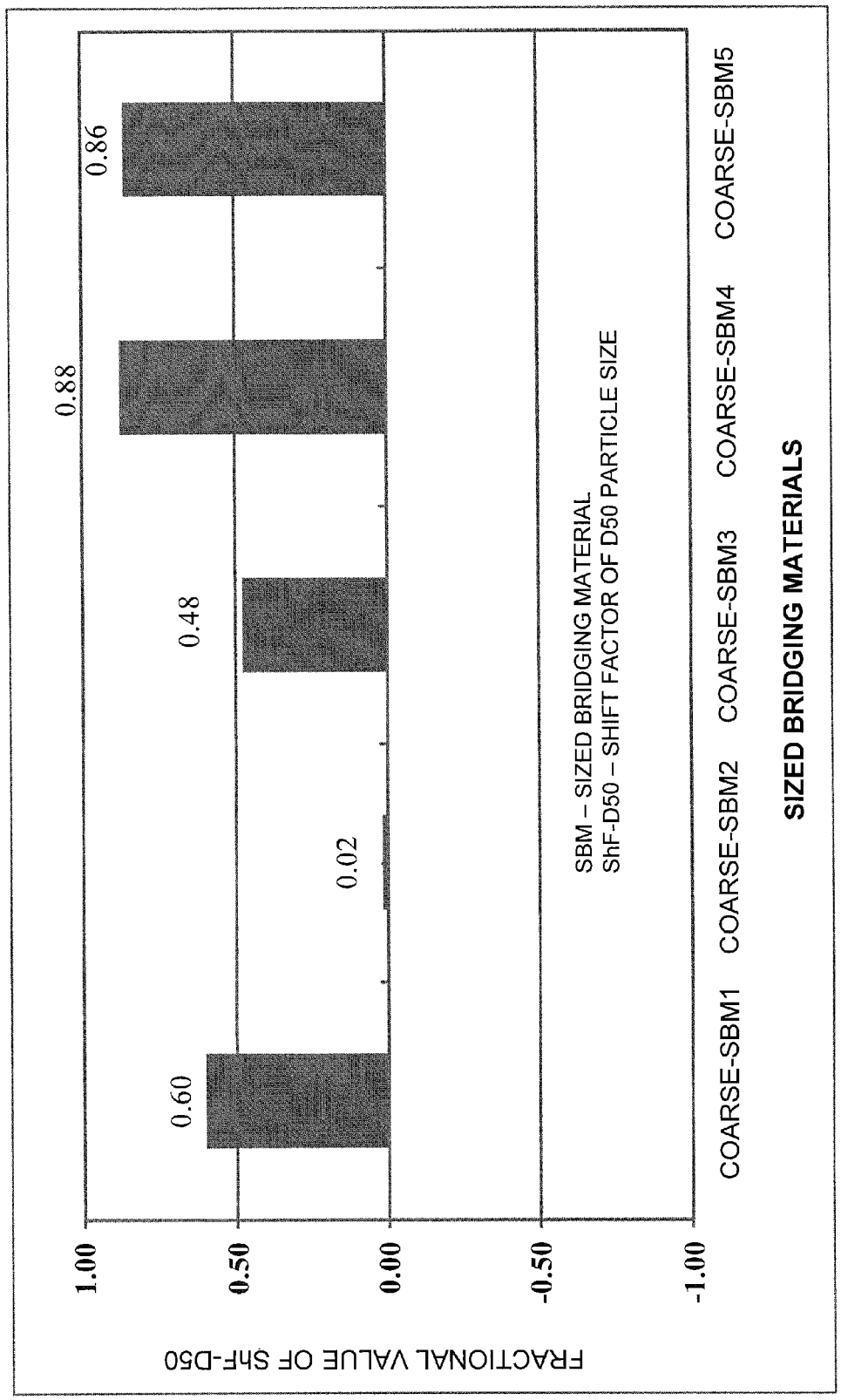

As shown in FIG. 8C, the Coarse-SBM4 sample has a high absolute value and a positive sign. This indicates that the Coarse-SBM4 sample had a large change in particle size and that the change was a net decrease in particle size. Thus, the Coarse-SBM4 sample exhibits poor particle strength. Unlike the Fine-SBM2 and the Medium-SBM2 samples, the Coarse-SBM4 sample will need frequent additions of the Coarse-SBM4 solids material to the drilling mud to maintain the desired particle distribution during wellbore operations. This may cause serious formation damage due to poor quality mudcake formed on the borehole wall. This is caused by a poor match between the degrading Coarse-SBM4 particle sizes and the reservoir pore size distribution. The poor quality mudcake will lead to higher spurt and fluid loss into the reservoir, creating a buildup of mudcake in the reservoir surrounding the wellbore. This may cause a serious reduction of the poro-perm characteristics of the wellbore reservoir formation creating flow problems in the reservoir surrounding the wellbore.

The D50 shift factor may be further used to classify batches of sized bridging materials as described below. A classified batch of sized bridging materials may then be used without further testing. This will allow an operator located at a drilling site to quickly and easily identify the appropriate sized bridging materials for use during drilling operations. Referring to FIG. 9, a classification system is disclosed. As described above, the D50 shift factor is a ratio of the difference in mass median diameter of the particles of a control sample of sized bridging material and the particles of a wet grinding sample of the same sized bridging materials to the mass median diameter of the particles of the control sample. Thus, the D50 shift factor will also have a value between −1 and 1, wherein values closer to 0 may be said to have a higher relative strength due to the smaller change in the mass median diameter between the samples. Experimentation indicated that the method described above produces a 2-3% variation between tested samples of the same batch and a maximum variation of 5%. Thus, a sized bridging material batch that produces a D50 shift factor no greater than 5% from the 0 value may be considered an extremely tough or strong sized bridging material. Similarly, a sized bridging material batch that produces a D50 shift factor no greater than 5% from the 1 or −1 value may be considered an extremely weak sized bridging material. By taking the absolute value of the D50 shift factor a classification table may be produced with a value range extending from 0 for an extremely tough sized bridging material to 1 for an extremely weak sized bridging material. Generally, tough or strong sized bridging materials may have a D50 shift factor that indicates a change in mass median diameter of less than 30%. Thus, sized bridging materials having D50 shift factor of 0 to 0.3 may be considered tough or strong sized bridging materials. Similarly, sized bridging materials having a D50 shift factor of 0.31 to 1 may be considered weak sized bridging materials. This allows for classification of all sized bridging materials into categories of tough sized bridging materials and weak sized bridging materials based on the criteria described above. Due to the relative homogeneity of the materials used to manufacture a particular batch of sized bridging materials, the test sample classification may be assigned to the entire batch from which the test sample was taken.

Based on the 5% determination described above, and as shown in FIG. 9, tough sized bridging materials may be further classified according to a plurality of rules in a rule base as follows. Sized bridging materials producing a D50 shift factor in the range of 0 to 0.05 may be classified as extremely tough, and an SBM-ET designation, sized bridging materials-extremely tough, may be assigned to the batch. Sized bridging materials producing a D50 shift factor greater than 0.5 and less than or equal to 0.1, i.e., in the range of 0.051 to 0.1, may be classified as very tough, and an SBM-VT designation, sized bridging materials-very tough, may be assigned to the batch. Sized bridging materials producing a D50 shift factor greater than 0.1 and less than or equal to 0.2, i.e., in the range of 0.11 to 0.2, may be classified as moderately tough, and an SBM-MT designation, sized bridging materials-moderately tough, may be assigned to the batch. Sized bridging materials producing a D50 shift factor greater than 0.2 and less than or equal to 0.3, i.e., in the range of 0.21 to 0.3, may be classified as slightly tough, and an SBM-ST designation, sized bridging materials-slightly tough, may be assigned to the batch.

In a similar manner, sized bridging materials producing a D50 shift factor greater than 0.9 and less than 1, i.e. in the range of 0.91 to 1, may be classified as extremely weak, and an SBM-EW designation, sized bridging materials-extremely weak, may be assigned to the entire batch. Sized bridging materials producing a D50 shift factor greater than 0.7 and less than or equal to 0.9, i.e., in the range of 0.71 to 0.9, may be classified as very weak, and an SBM-VW designation, sized bridging materials-very weak, may be assigned to the entire batch. Sized bridging materials producing a D50 shift factor greater than 0.5 and less than or equal to 0.7, i.e., in the range of 0.51 to 0.7, may be classified as fairly weak, and an SBM-FW designation, sized bridging materials-fairly weak, may be assigned to the entire batch. Sized bridging materials producing a D50 shift factor greater than 0.3 and less than or equal to 0.5, i.e., in the range of 0.31 to 0.5, may be classified as weak, and an SBM-W designation, sized bridging materials-weak, may be assigned to the entire batch.

Once a D50 shift factor is determined in accordance with the method described above, an absolute value of the D50 shift factor may be taken. By taking the absolute value of the D50 shift factor, the D50 shift factor for any particular tested sized bridging material may be compared to the classification system of FIG. 9 to determine a classification for the batch from which the test samples were taken. By assigning a classification to the batch from which the test sample was taken, the classification scheme provides a reliable qualitative guiding tool to mud technicians, mud engineers, mud consultants, and drilling engineers to identify, select, and use the appropriate sized bridging materials for high performance drill-in fluid design.

In an exemplary embodiment, the Fine-SBM4 sample of FIG. 8A had a D50 shift factor of −0.54, indicating that the Fine-SBM4 sample increased in mass median diameter during the wet grinding process. This sample may be classified by first taking the absolute value of the Fine-SBM4 shift factor to get a 0.54 classification D50 shift value. This value may be compared to the chart on FIG. 9 to determine the classification of the Fine-SBM4 sample. As shown on FIG. 9, a D50 shift factor of 0.54 correlates to a Fairly Weak designation; thus, the Fine-SBM4 batch from which the tested sample was taken may be classified as SBM-FW. This classification will allow operators dealing with the Fine-SBM4 batch to quickly and accurately determine the suitableness of the Fine-SBM4 batch for use in their drilling operations.

In an another exemplary embodiment, the Coarse-SB2 sample of FIG. 8C had a D50 shift factor of 0.02, indicating that the Coarse-SBM2 sample decreased in mass median diameter during the wet grinding process, but only slightly. This sample may be classified by first taking the absolute value of the Coarse-SBM2 shift factor to get a 0.02 classification D50 shift value. This value may be compared to the chart on FIG. 9 to determine the classification of the Coarse-SBM2 sample. As shown on FIG. 9, a D50 shift factor of 0.02 correlates to an Extremely Tough designation; thus, the Coarse-SBM2 batch from which the tested sample was taken may be classified as SBM-ET. This classification will allow operators dealing with the Coarse-SBM2 batch to quickly and accurately determine the suitableness of the Coarse-SBM2 batch for use in their drilling operations.

Accordingly, the disclosed embodiments provide a classification scheme that may be used as a reliable tool to assess the quality of all sized bridging materials available for drilling, drill-in, and completion fluid design. In addition, the disclosed classification scheme provides a comprehensive ranking of sized bridging materials that gives a meaningful context for selection and use of sized bridging materials by mud technicians, mud engineers, mud chemists, drilling engineers, mud consultants, and the like.

Ranges may be expressed herein as from about one particular value, and/or to about another particular value. When such a range is expressed, it is to be understood that another embodiment is from the one particular value and/or to the other particular value, along with all combinations within said range.

It is understood that the present invention may take many forms and embodiments. Accordingly, several variations may be made in the foregoing without departing from the spirit or scope of the invention. Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

What is claimed is:

1. A method for selecting sized bridging materials for use in drill-in fluid, the method comprising the steps of:
    (a) obtaining amounts of sized bridging materials having different properties;
    (b) obtaining absolute values of D50 shift properties of the amounts of sized bridging material;
    (c) comparing the absolute values of the D50 shift properties of the amounts of sized bridging materials with a classification system to determine classifications for the amounts of sized bridging materials; and
    (d) determining the suitability of adding the sized bridging material to drilling mud that is being used to drill a well based on the determined classification.

2. The method of claim 1 further comprising testing a sample of a different sized bridging material to determine a durability metric for the sample.

3. The method of claim 1, wherein the sized bridging material comprises particles that are coarse, medium, and fine.

4. The method of claim 3, wherein the sized bridging material added to the drilling fluid is limited to sized bridging material having an absolute value of D50 shift that is less than 0.3.

5. The method of claim 1, wherein the sized bridging material added to the drilling fluid is limited to sized bridging material having an absolute value of D50 shift that is less than 0.2.

6. The method of claim 5, wherein the sized bridging material added to the drilling fluid is limited to sized bridging material having an absolute value of D50 shift that is less than 0.1.

7. The method of claim 6, wherein the sized bridging material added to the drilling fluid is limited to sized bridging material having an absolute value of D50 shift that is less than 0.05.

8. The method of claim 1, further comprising identifying sized bridging material having an absolute value of C shift that is greater than 0.3 to define weak sized bridging material.

9. A method for identifying a relative strength of bridging materials for use in drill-in fluid comprising:
    (a) sizing a sample of the bridging material to produce a control particle size distribution of the bridging material;
    (b) disposing an amount of the sample of the bridging material and a liquid in a tubular container;
    (c) rotating the tubular container having the sample of the bridging material and liquid;
    (d) removing a portion of the sample of the bridging material and liquid from the tubular container;
    (e) analyzing an amount of the sample of the bridging material and liquid that were removed from the tubular container to measure the size of particles of the portion of the sample of the bridging material removed from the tubular container, and to produce a particle size distribution of the amount of the sample of the bridging material removed from the tubular container;

(f) comparing the particle size distribution of the bridging material with the particle size distribution of the amount of the sample of the bridging material removed from the tubular container to determine a value of a $D50$ shift factor to obtain a tested sized bridging material;

(g) comparing absolute values of the $D50$ shift properties of the amounts of bridging materials with a classification system to determine classifications for the amounts of sized bridging materials; and (h) determining the suitability of adding the bridging material to drilling mud that is being used to drill a well based on the determined classification.

10. The method of claim 9 further comprising, comparing the $D50$ shift factor for the sized bridging material to a set of rules in a rule base, the rules corresponding to a relative strength of the sized bridging material for use in drill-in fluid; when a match is found between a particular one of the set of rules in the rule base and the tested sized bridging material, determining a relative strength for the tested sized bridging material that correlates to the particular rule in the rule base; and associating the tested sized bridging material with the relative strength correlating to the particular rule in the rule base.

11. The method of claim 10, wherein the set of rules in the rule base define subsets of the high relative strength classification comprising:
   an extremely tough strength correlating to a $D50$ shift factor of 0 to 0.05;
   a very tough strength correlating to a $D50$ shift factor of 0.051 to 0.1;
   a moderately tough strength correlating to a $D50$ shift factor of 0.11 to 0.2; and
   a slightly tough strength correlating to a $D50$ shift factor of 0.21 to 0.3.

12. The method of claim 9, wherein the set of rules in the rule base define a low relative strength having a $D50$ shift factor in the range of 0.31 to 1.0.

13. The method of claim 12, wherein the set of rules in the rule base define subsets of the low relative strength classification comprising:
   a weak strength rating correlating to a $D50$ shift factor of 0.31 to 0.5;
   a fairly weak strength rating correlating to a $D50$ shift factor of 0.51 to 0.7;
   a very weak strength rating correlating to a $D50$ shift factor of 0.71 to 0.9; and
   an extremely weak strength rating correlating to a $D50$ shift factor of 0.91 to 1.0.

14. A method for identifying a relative strength of sized bridging materials for use in drill-in fluid comprising:
   (a) testing a sample of a batch of sized bridging material to determine an absolute value of a $D50$ shift factor to obtain tested sized bridging material;
   (b) comparing the $D50$ shift factor for the sized bridging material to a set of rules in a rule base, the rules corresponding to a relative strength of the sized bridging material for use in drill-in fluid;
   (c) when a match is found between a particular one of the set of rules in the rule base and the tested sized bridging material, determining a relative strength for the tested sized bridging material that correlates to the particular rule in the rule base;

(d) associating the tested sample sized bridging material with the relative strength correlating to the particular rule in the rule base; and (e) assigning a classification rating to the batch of sized bridging materials from which the sample was selected.

15. The method of claim 14, wherein the set of rules in the rule base define a high relative strength having a $D50$ shift factor of 0.3 or less and wherein the $D50$ shift factor is a comparison of a $D50$ control value that is based on a size of particles from a preselected mass sample of sized bridging materials suspended in a test volume of fluid and a $D50$ wet grinding value.

16. The method of claim 15, wherein the set of rules in the rule base define subsets of the high relative strength classification comprising:
   an extremely tough strength correlating to a $D50$ shift factor of 0 to 0.05;
   a very tough strength correlating to a $D50$ shift factor of 0.051 to 0.1;
   a moderately tough strength correlating to a $D50$ shift factor of 0.11 to 0.2; and
   a slightly tough strength correlating to a $D50$ shift factor of 0.21 to 0.3.

17. The method of claim 16, wherein step (e) comprises:
   assigning an SBM-ET rating in the event the batch has the extremely tough strength correlating to a $D50$ shift factor of 0 to 0.05;
   assigning an SBM-VT rating in the event the batch has the very tough strength correlating to a $D50$ shift factor of 0.051 to 0.1;
   assigning an SBM-MT rating in the event the batch has the moderately tough strength correlating to a $D50$ shift factor of 0.11 to 0.2; and
   assigning an SBM-ST rating in the event the batch has the a slightly tough strength correlating to a $D50$ shift factor of 0.21 to 0.3.

18. The method of claim 14, wherein the set of rules in the rule base define a low relative strength having a $D50$ shift factor of 0.31 or greater.

19. The method of claim 18, wherein the set of rules in the rule base define subsets of the low relative strength classification comprising:
   a weak strength rating correlating to a $D50$ shift factor of 0.31 to 0.5;
   a fairly weak strength rating correlating to a $D50$ shift factor of 0.51 to 0.7;
   a very weak strength rating correlating to a $D50$ shift factor of 0.71 to 0.9; and
   an extremely weak strength rating correlating to a $D50$ shift factor of 0.91 to 1.

20. The method of claim 19, wherein step (e) comprises:
   assigning an SBM-W rating in the event the batch has the weak strength rating correlating to a $D50$ shift factor of 0.31 to 0.5;
   assigning an SBM-FW rating in the event the batch has the fairly weak strength rating correlating to a $D50$ shift factor of 0.51 to 0.7;
   assigning an SBM-VW rating in the event the batch has the very weak strength rating correlating to a $D50$ shift factor of 0.71 to 0.9; and
   assigning an SBM-EW rating in the event the batch has the extremely weak strength rating correlating to a $D50$ shift factor of 0.91 to 1.

* * * * *